(12) United States Patent
Fabrizio et al.

(10) Patent No.: US 11,197,658 B2
(45) Date of Patent: Dec. 14, 2021

(54) COLLECTION AND TREATMENT OF A BIOFLUID SAMPLE

(71) Applicant: NANOBIO SYSTEMS INC., Marblehead, MA (US)

(72) Inventors: Eve F. Fabrizio, Avon, OH (US); Bindi Patel, Westlake, OH (US); Pamela Hendrix, Sandusky, OH (US); Kraig Holler, Fairview Park, OH (US); Jessica Klein, Chippewa Lake, OH (US); Trevor Zitek, Amherst, OH (US); Seyamak Keyghobad, Marion, MA (US)

(*) Notice: Subject to any disclaimer, the term of this patent is extended or adjusted under 35 U.S.C. 154(b) by 0 days.

(21) Appl. No.: 17/055,764

(22) PCT Filed: Apr. 18, 2019

(86) PCT No.: PCT/US2019/028080
§ 371 (c)(1),
(2) Date: Nov. 16, 2020

(87) PCT Pub. No.: WO2019/221872
PCT Pub. Date: Nov. 21, 2019

(65) Prior Publication Data
US 2021/0228190 A1 Jul. 29, 2021

Related U.S. Application Data

(60) Provisional application No. 62/673,446, filed on May 18, 2018, provisional application No. 62/820,455, filed on Mar. 19, 2019.

(51) Int. Cl.
*G01N 1/00* (2006.01)
*A61B 10/00* (2006.01)
(Continued)

(52) U.S. Cl.
CPC .... *A61B 10/0051* (2013.01); *A61B 5/150022* (2013.01); *A61B 5/150755* (2013.01);
(Continued)

(58) Field of Classification Search
None
See application file for complete search history.

(56) References Cited

U.S. PATENT DOCUMENTS 9,816,087 B2 11/2017 Gellibolian et al.
2001/0023324 A1 9/2001 Pronovost et al.
(Continued)

FOREIGN PATENT DOCUMENTS

WO 2018223101 A1 12/2018

OTHER PUBLICATIONS

International Search Report and Written Opinion dated Jul. 12, 2019 for Application No. PCT/US2019/028080.

*Primary Examiner* — Jyoti Nagpaul
(74) *Attorney, Agent, or Firm* — Tarolli, Sundheim, Covell & Tummino LLP

(57) ABSTRACT

A system can facilitate pre-treatment a biofluid sample for various applications for monitoring and/or tracking a subject's health. The system includes a sample collection component that can collect the biofluid sample. The system also includes a mixing component that includes a media with a material. Upon adding the biofluid sample to the mixing component, the biofluid sample mixes with the media. The system also includes a filter component that can filter the media from the biofluid sample. After the media is filtered from the biofluid sample, the biofluid sample can be provided to an analyte analysis application.

20 Claims, 9 Drawing Sheets

(51) Int. Cl.
*A61B 5/15* (2006.01)
*G01N 1/28* (2006.01)
*G01N 1/38* (2006.01)
*G01N 1/40* (2006.01)

(52) U.S. Cl.
CPC ........... *A61B 10/007* (2013.01); *G01N 1/286* (2013.01); *G01N 1/38* (2013.01); *G01N 1/405* (2013.01); *A61B 2010/0067* (2013.01)

(56) References Cited

U.S. PATENT DOCUMENTS

| | | |
|---|---|---|
| 2010/0049016 A1 | 2/2010 | Aronowitz et al. |
| 2010/0173394 A1* | 7/2010 | Colston, Jr. ......... B01F 13/0062 435/287.2 |

* cited by examiner

COLLECTION AND TREATMENT OF A BIOFLUID SAMPLE

RELATED APPLICATIONS

This application claims priority to U.S. Provisional Application Ser. No. 62/673,446, filed May 18, 2018, and entitled "SALIVA COLLECTION AND TREATMENT". This application also claims priority to U.S. Provisional Application Ser. No. 62/820,455, filed Mar. 19, 2019, and entitled "SALIVA COLLECTION AND TREATMENT". These provisional applications are hereby incorporated by reference in their entirety for all purposes.

TECHNICAL FIELD

The present disclosure relates generally to collection and treatment of a biofluid sample, and, more specifically, to systems and methods that collect and treat the biofluid sample in preparation for a diagnostic, tracking, and/or monitoring application.

BACKGROUND

Saliva is a biofluid that aids in swallowing and digestion. While saliva is mostly composed of water, saliva also includes key biomarkers (or analytes) that can be used to diagnose and/or monitor a subject's health and wellness, as well as additional components (including bacteria, mycoplasma, enzymes, proteins, electrolytes, and the like) that can bind to or break down the key biomarkers. The analytes (including salivary glucose, which can be monitored and tracked as an analog to blood glucose) can be consumed by bacteria and mycoplasma in saliva, making their detection in a saliva sample difficult. Additionally, electrolytes, like thiocyanate, in saliva can react with hydrogen peroxide, making it difficult to use hydrogen peroxide based enzymatic sensors for the detection of the analytes. Accordingly, to detect these analytes in saliva in a stable and reliable fashion, the saliva must be pre-treated to minimize or eliminate the additional components that have a negative effect the analyte or the detection of the analyte.

SUMMARY

The present disclosure relates to systems and that facilitate collect and treat a biofluid sample in preparation for a diagnostic, tracking, and/or monitoring application.

In one aspect, the present disclosure can include a system that collects and treats a biofluid sample in preparation for a diagnostic, tracking, and/or monitoring application. The system includes a sample collection component that can be configured to collect a biofluid sample. The system also includes a mixing component that includes a media with a material. The mixing component can be configured such that upon adding the biofluid sample to the mixing component, the biofluid sample mixes with the media. The system also includes a filter component that can be configured to filter the media from the biofluid sample. After the media is filtered from the biofluid sample, the biofluid sample can be provided to an analyte analysis application.

In another aspect, the present disclosure can include a method for collecting and treating a biofluid sample in preparation for a diagnostic, tracking, and/or monitoring application. A biofluid sample including water, an analyte, and one or more additional components that have a negative effect on detection of the analyte in the biofluid sample can be collected. The biofluid sample can be added to a media that includes a material. The biofluid sample and the media can be mixed so that the media can eliminate at least a portion of the at least one additional component from the biofluid sample. The media can then be filtered from the biofluid sample. Notably, the filtering and mixing each use a mechanical mechanism. The biofluid sample can be provided for analysis to detect the analyte in the biofluid sample.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
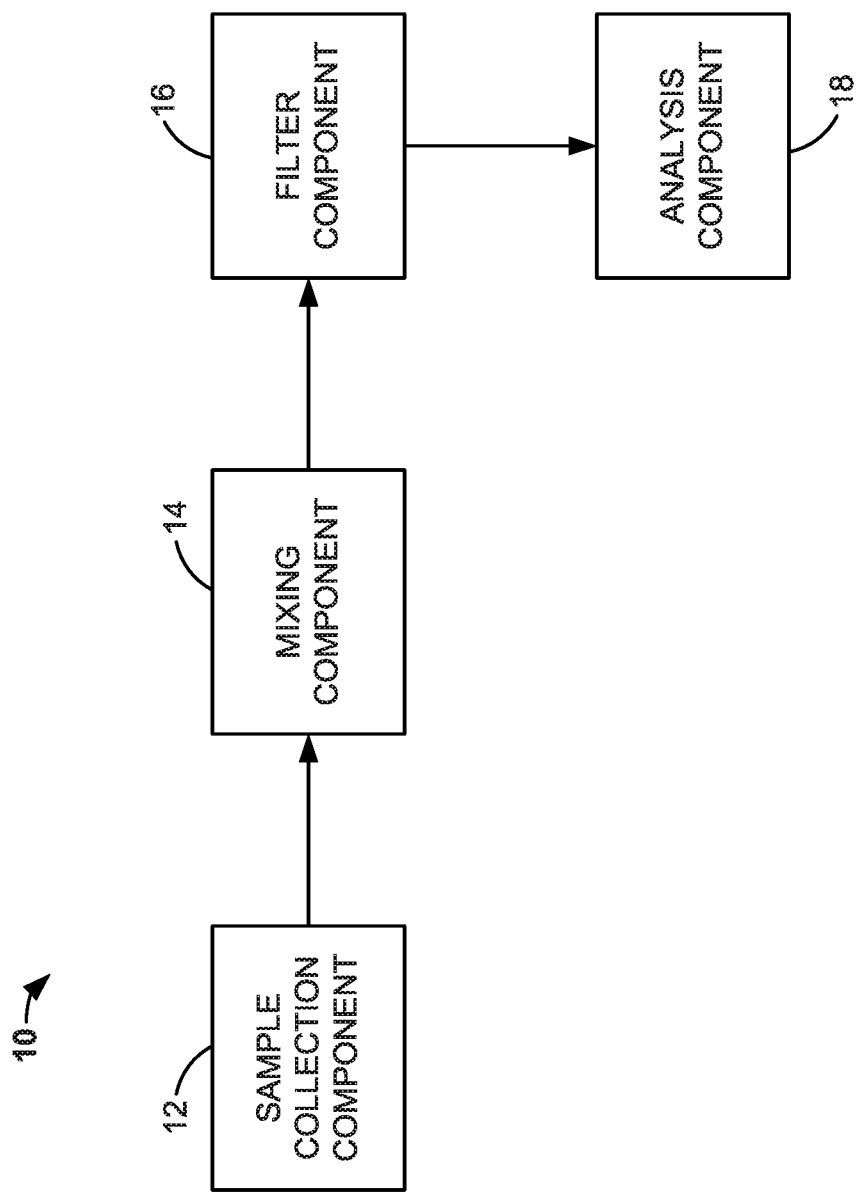
FIG. 1 is a block diagram showing an example of a system collects and treats a biofluid sample in preparation for a diagnostic, tracking, and/or monitoring application.

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "sample" refers to a volume of a specimen (e.g., a biofluid) taken for testing or analysis.

As used herein, the term "biofluid" refers to any biological fluid originating from a subject or patient. The biofluid can be, for example, saliva, sweat, tears, interstitial fluid, blood, urine, or the like. The biofluid can include water, an analyte, and one or more additional components.

As used herein, the term "analyte" refers to a substance whose chemical constituents are being identified and measured. The analyte can be a key biomarker for a certain medical condition that can be used to diagnose and/or monitor a subject's health and wellness.

As used herein, the term "additional component" refers to any substance within a biofluid other than the water and the analyte. The additional components of the biofluid may bind to or break down an analyte in the biofluid and/or have a negative effect on detection of the analyte in the biofluid. The additional components in the biofluid can include organisms (e.g., bacteria or any other organism that contains a cell membrane or other fatty acid structure), mycoplasma, enzymes, proteins, electrolytes, food particles, and the like. In some instances, one or more of the additional components can be referred to as "contaminants" that contaminate the biofluid sample for detection of the analyte.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure generally relates to detecting an analyte in a biofluid sample to diagnose, monitor and/or track a subject's health. The biofluid sample can include water, the analyte, and additional components. One or more of the additional components may impede detection of the analyte in the biofluid sample by binding to and/or breaking down the analyte. Additionally or alternatively, the one or more of the additional components may otherwise have a negative affect on detection of the analyte, thereby negatively affecting the detection of the analyte. Advantageously, the present disclosure sets forth systems and methods that facilitate pre-treatment of a biofluid sample in preparation for analyte detection applications that can be used to diagnose, monitor, and/or track a subject's health and wellness.

The systems and methods described herein provide a collection and treatment process for a biofluid sample. The collection and treatment process eliminates additional components from the biofluid sample, allowing one or more analytes of interest to remain stable. As an example, the biofluid can be saliva, the analyte of interest can be glucose, and the additional components can be organisms (e.g., bacteria), mycoplasma, enzymes, etc. After undergoing the collection and treatment process, the analyte of interest can be detected within the biofluid more easily using any potential detection mechanism (including, but not limited to, colorimetric assays, photometric assays, and/or electrochemical assays, such as, amperometric assays, voltammetric assays, coulometric assays, and the like). The pre-treatment process is especially helpful for detection mechanisms that utilize an enzyme based process where the additional components interact with the enzymatic byproducts, the additional components provide a high background signal, and/or the additional components that vary viscosity of the biofluid sample.

III. Systems

One aspect of the present disclosure can include a system 10 (FIG. 1) that can collect and treat a biofluid sample in preparation for a diagnostic, tracking, and/or monitoring application. Generally, the biofluid sample (e.g., a bodily fluid, such as tears, saliva, urine, serum, plasma, blood, and the like) can include water, the analyte, and one or more additional components. Some of the one or more additional components can have a negative effect on detection of the analyte within the biofluid sample. The system 10 can remove at least a portion of these additional components to improve detection of the analyte.

The system 10 provides an easy to use, noninvasive or minimally invasive biofluid collection and pre-treatment mechanism that can be used in connection with an at-home and/or point of care screening tool (or "analysis component 18") that detects the analyte within the biofluid sample. The system 10 includes at least a sample collection component 12 and a sample treatment component. The sample collection component 12 can be used to collect the biofluid sample from a subject. After collection, the biofluid sample can be passed to the sample treatment component, which includes a mixing component 14 and a filter component 16. The mixing component 14 and the filter component 16 can work together to remove at least a portion of the one or more additional components from the biofluid sample. After treatment, the biofluid sample can be sent to the analysis component 18 for analyte detection. The analysis component 18 can include one or more devices to detect the analyte within the treated biofluid sample. With the portion of the one or more analytes removed from the biofluid sample, the detection of the analyte by the analysis component 18 can be much improved.

The sample collection component 12 can be configured to collect the biofluid sample passively and/or actively. For passive collection, the saliva collection component 12 can include a cup, a bag, or other such mechanism to receive biofluid that has been expelled from a subject's body. When used for active collection, the saliva collection component 12 can include a collection device that can be placed at or near a source of the biofluid. For example, active collection can be accomplished using a swab, a foam, or another type of absorptive fluid collection device and/or a suction device.

After collection, the biofluid sample can be passed to the mixing component 14. The mixing component 14 can facilitate a mixing between the biofluid sample and a media. The biofluid sample and the media can be allowed to interact within the same housing for a time (which depends on the particular media, analyte, and/or the one or more additional components), where the media can remove at least the portion of the at least one additional component from the biofluid sample (e.g., through adsorption). The configuration of the media can be chosen based on the biofluid, the analyte, and/or the one or more additional components.

The media can include at least one of a ceramic, a metal, a foam, a paper, or the like. In some instances, the media can contain pores and the pore size and density can be selected to enhance the adsorption of certain unwanted species or interferants. Additionally or alternatively, the media can include an additional material that can facilitate the removal at least the portion of the at least one additional component. In some instances, the additional material can be bound within and/or bound to at least a portion of the media. In other instances, the media can be the additional material. The additional material can include carbon (e.g., activated charcoal, activated carbon, carbon black, graphite, graphene, oxidized graphene, and/or reduced graphene), which can remove one or more additional components with a cell membrane or other fatty acid structure from the biofluid sample. The additional material can, additionally or alternatively, include a different material (other than carbon) that can facilitate ion exchange with the biofluid sample to inhibit at least another portion of the one or more additional component (e.g., having a strong base anion type 1).

After a period of mixing, the biofluid sample and the media can pass through a filter component 16. The filter component 16 can be configured to filter (or separate) the media from the biofluid sample. As an example, the filter component 16 can include one or more physical filter membranes where the biofluid can pass through and the media cannot pass through (e.g., with a pore size less than a certain value based on the one or more additional components being removed; in many instances, the pore size should be less than or equal to 1 μm). The physical filter membrane can be, for example, cellulose acetate (CA), polyvinylidene fluoride (PVDF), Teflon, nylon, paper, and/or glass. It should be noted that the mixing component 14 and/or the filter component 16 can employ a mechanical mechanism to facilitate the mixing and/or the filtering, respectively. The mechanical mechanism can be centrifugal force, pressure, and/or flow. After the media is filtered from the biofluid sample, the filtered biofluid sample can be provided to an analysis component 18, which can detect the analyte in the biofluid sample.

IV. Methods

Figure 2:
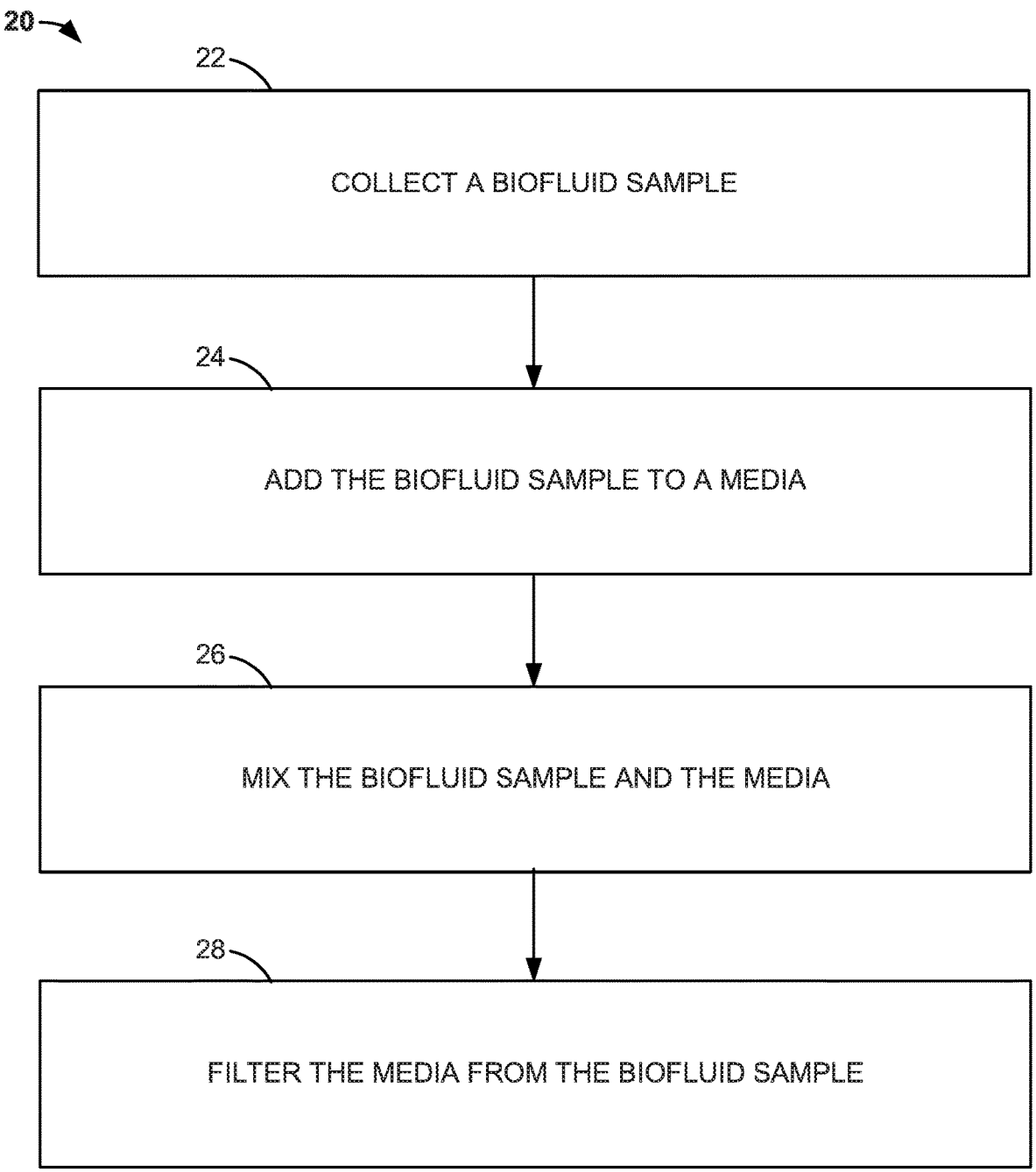
FIG. 2 is a process flow diagram showing an example method for collecting and treating a biofluid sample in preparation for a diagnostic, tracking, and/or monitoring application.

Another aspect of the present disclosure can include a method 20 (FIG. 2) for collecting and treating a biofluid sample in preparation for a diagnostic, tracking, and/or monitoring application. As an example, the method 20 can be executed using the system 10 shown in FIG. 1 and described above. Advantageously, the method 20 can be used to remove one or more additional components from the biofluid sample to enhance the detection of the analyte.

The method 20 is illustrated as a process flow diagram with flowchart illustrations. For purposes of simplicity, the method 20 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 20.

At Step 22, a biofluid sample can be collected (e.g., by sample collection component 12). The biofluid sample can include water, an analyte, and at least one additional component that has a negative effect on detection of the analyte in the biofluid sample. In some instances, the biofluid sample can include a bodily fluid, such as tears, saliva, urine, serum, plasma, and/or blood. The biofluid sample can be collected in a passive way (through passive expulsion from a subject's body) or an active way (at or near a source of the biofluid).

At Step 24, the biofluid sample can be added to a media (e.g., within a mixing component 14). For example, the biofluid sample and the media can be added to the same housing and allowed to interact for a time. At Step 26, the biofluid sample and the media are mixed (e.g., within the mixing component). The media eliminates at least a portion of the at least one additional component from the biofluid sample. In some instances, a material can be bound within and/or bound to the media to facilitate removal of at least one additional component from the biofluid sample and/or to facilitate ion exchange with the biofluid sample to inhibit at least another additional component. The material can be embodied in, bound to and/or bound within at least a portion of the media. As an example, at least the portion of the media can include at least one of a ceramic material, a metallic material, and a paper material.

At Step 28, the media can be filtered from the biofluid sample (e.g., by a filter component 16, which can include any number of filters). In some instances, the media and the biofluid sample can be passed through a physical filter membrane to remove the media from the biofluid sample. The physical filter membrane can include cellulose acetate (CA), polyvinylidene fluoride (PVDF), Teflon, nylon, paper, and/or glass. It should be noted that the mixing and/or the filtering can use a mechanical mechanism, such as centrifugal force and/or flow to facilitate the mixing and/or the filtering. The filtered biofluid sample can be provided to one or more detection devices (e.g., analysis component 18) for analysis to detect the analyte within the biofluid sample. The analysis includes detection of the analyte in the biofluid sample. In some instances, the detection can use an enzyme-based process, which can detect an amount of the analyte in the biofluid sample using a colorimetric detection mechanism, a photometric detection mechanism, and/or an electrochemical detection mechanism.

V. Proposed Configuration of Sample Collection and Treatment Device

Figure 3:
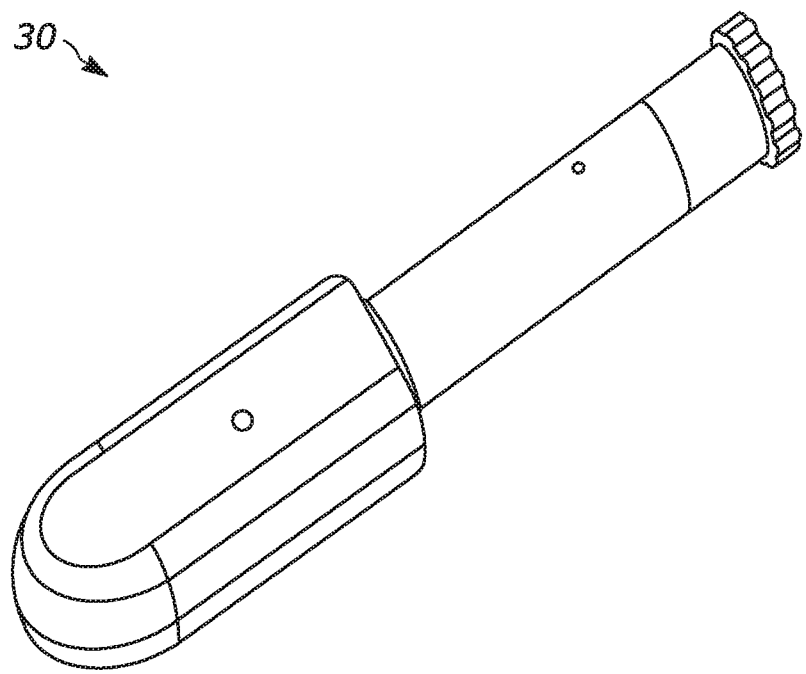
FIGS. 3-5 are different exterior views of an example saliva collection and treatment device.
Figure 4:
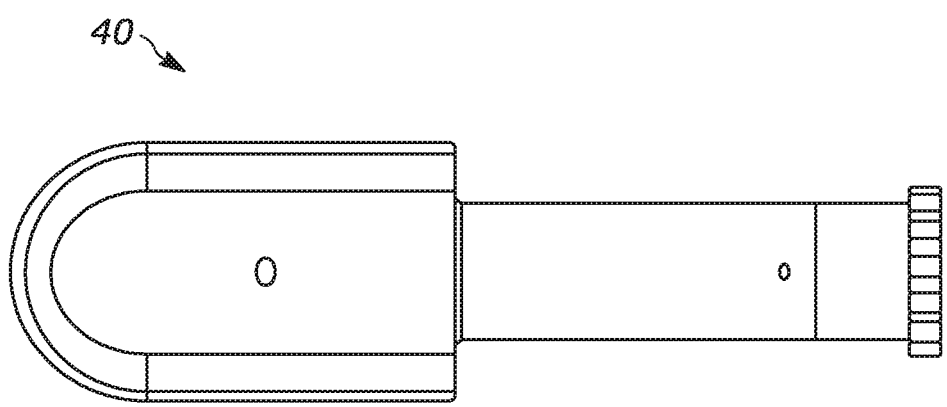
Figure 5:
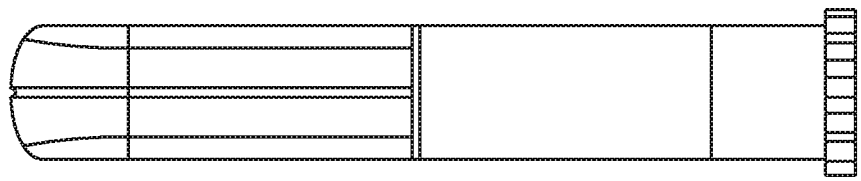
Figure 6:
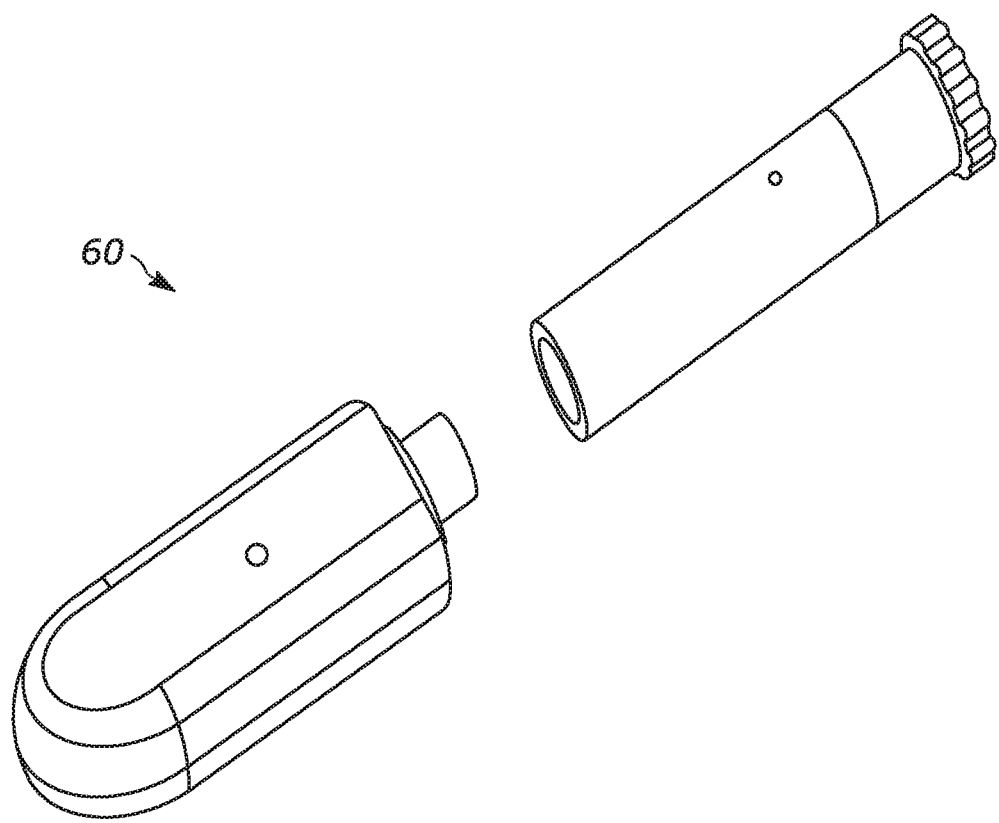
FIGS. 6-9 are different views of the interior of example saliva and treatment device.
Figure 7:
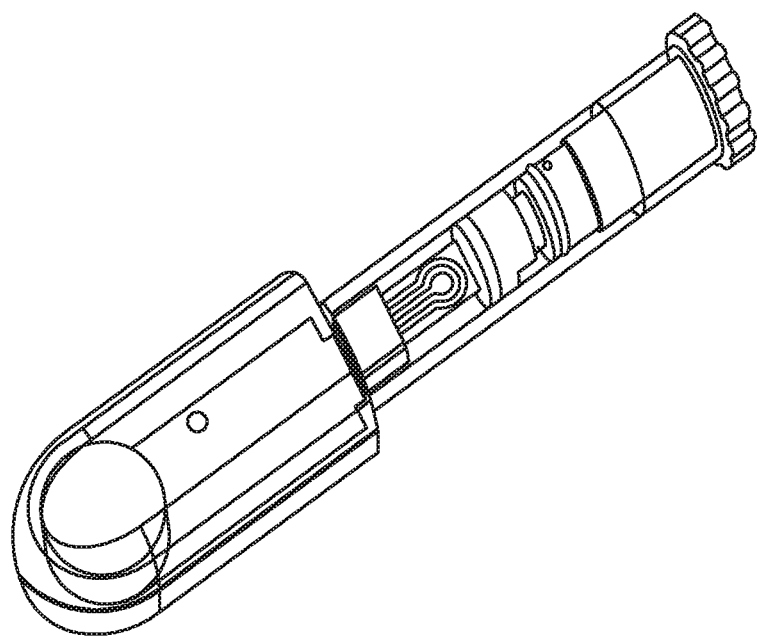
Figure 8:
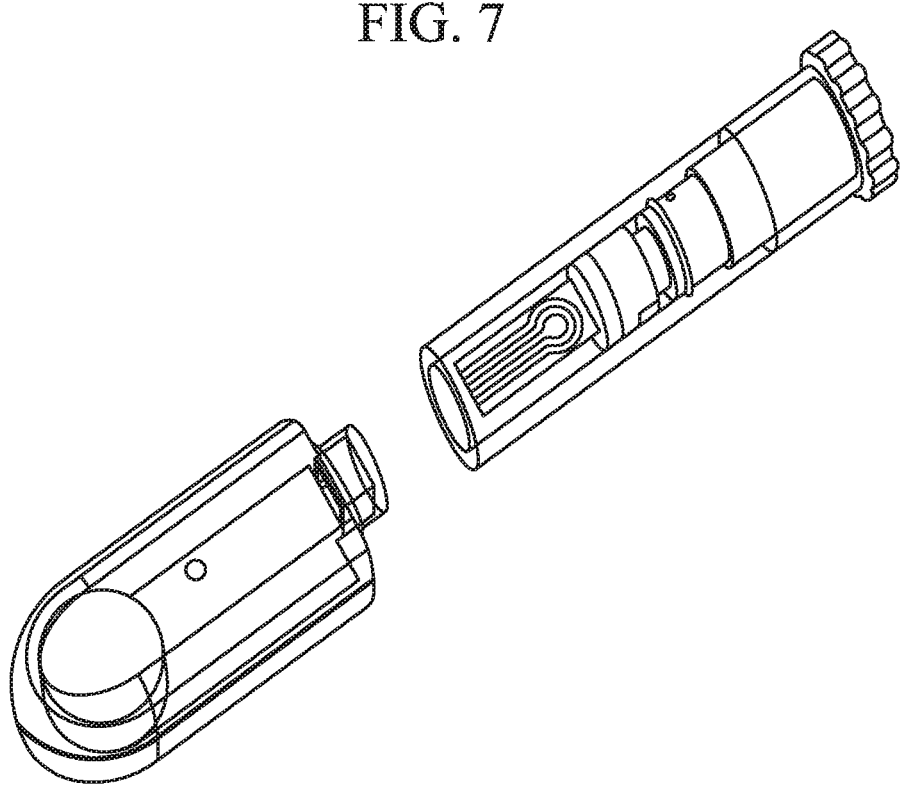
Figure 9:
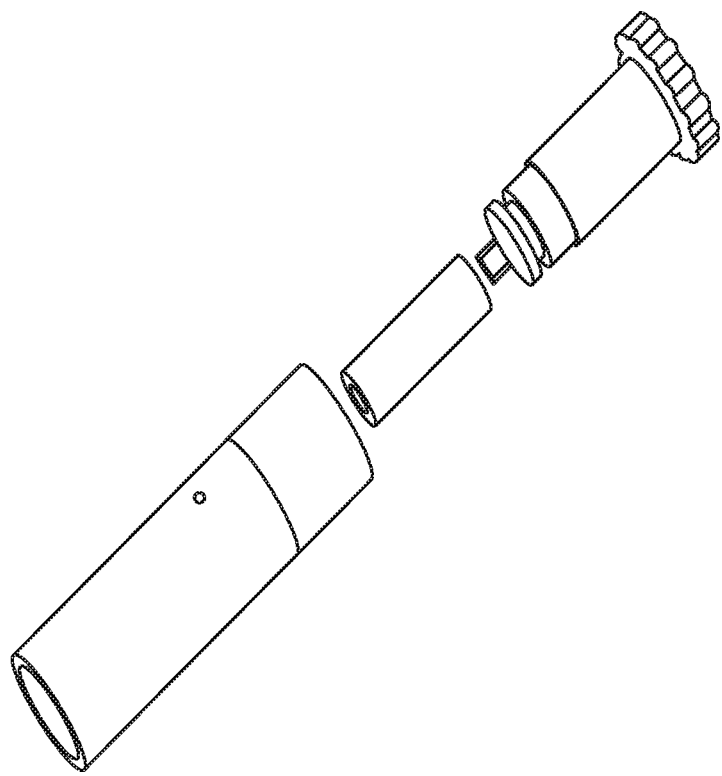

FIGS. 3-9 are schematic diagrams showing different views of a proposed sample collection and treatment device (the "device") that can be employed by the system 10 and/or method 20. FIGS. 3-5 are a perspective view, a front view, and a side view of the exterior of the sample treatment device. FIG. 6 shows the device in open form. FIGS. 7-9 show the interior of the device.

The device includes a screw plunger a main housing barrel, a sieve-mixing barrel, a final filter, and a sensor deposit area. A collection swab can be placed in the main housing barrel and compressed by the screw plunger to drain the saliva. Charcoal can be placed within the sieve-mixing barrel. A sensor can be placed in the sensor deposit area. The sensor can receive treated saliva that has been run through the device.

VI. Example Design Considerations

The following example illustrates considerations that can be used when designing a biofluid collection and treatment device. In this example, the biofluid is saliva.

Properties of Saliva

A device that can be used for collection and treatment of saliva must accommodate the following properties of saliva.
Viscosity—ranging from 2 cP to 10 cP
Density—1.0 mg/mL (since saliva is 98% water, same density as water)
Conductivity—ranging from 4 mS to 6 mS
Device Component Requirements
The device requires the following components.
Saliva Collection Swab—Salimetrics Saliva Bio Oral Swab (SOS)
Activated Charcoal (AC)—Mesh 4-20 (particle size diameter 500 μm to 1 mm) from coconut shells
Post AC Filter—0.22 μm, surfactant free, low protein binding, cellulose acetate (CA). Polyvinylidene difluoride (PVDF) and nylon can also be used.

Housing (for device and components within the device)—polypropylene, non-toxic, pyrogen free Key Design Considerations for Device The device has the following design considerations.

Maximum Volume Collected by Swab—1.3 mL or 1.5 mg of saliva

AC to Saliva Ratio—18 mg to 1 mg (AC must be 18× greater than saliva)

Volume Needed for AC—no greater than 8 cubic mm

Exposure Time of Saliva to AC with Mixing—30 seconds (vortex mixing or turbulent mixing)

Final Volume of Treated Saliva—40 µL-60 µL

Saliva may be exposed to air to maintain oxygen levels.

VI. Example Showing the Collection and Treatment of Human Saliva

The following Example shows a collection and treatment process that can stabilize glucose in a saliva sample for up to two hours after collection. The collection and treatment process also eliminates issues with rapid degradation of hydrogen peroxide, leading to well behaved detection of glucose in saliva.

The collection and treatment process involves collecting saliva as passive drool or with a swab, cotton, or foam. After collection, the saliva sample ("the sample") is immediately added to a carbon-based material, such as activated charcoal, into a 1.5 mL Eppendorf tube. Vortexing is applied for a brief period to mix the sample and the activated charcoal. Then the sample is filtered through a 0.22 µm filter disk to hold back activated charcoal and/or larger molecular weight species.

Figure 10:
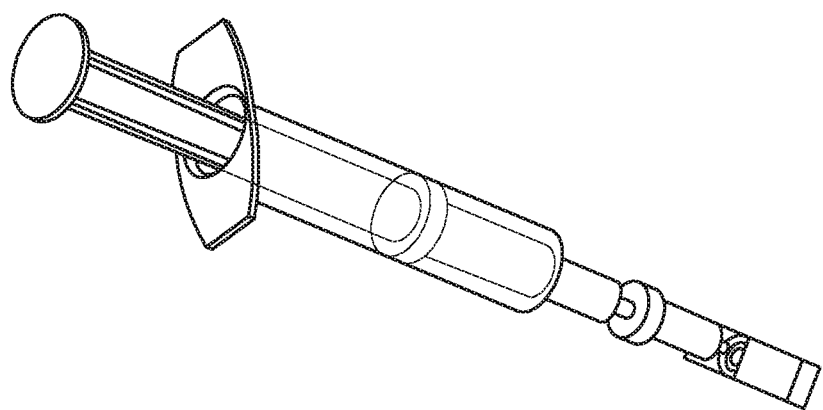
FIG. 10 is a photograph of another example saliva collection and treatment device.

FIG. 10 shows a prototype of a device used in the collection and treatment process. The sample is added to the top of a syringe (e.g., as shown, a swab can be placed inside the syringe barrel), which has a 900 µL spin column attached to the outlet of the syringe. The spin column contains activated charcoal and a filter disk to hold back the activated charcoal and larger molecular species. The treated sample can be placed on a sensing device to detect glucose within the saliva.

Figure 12:
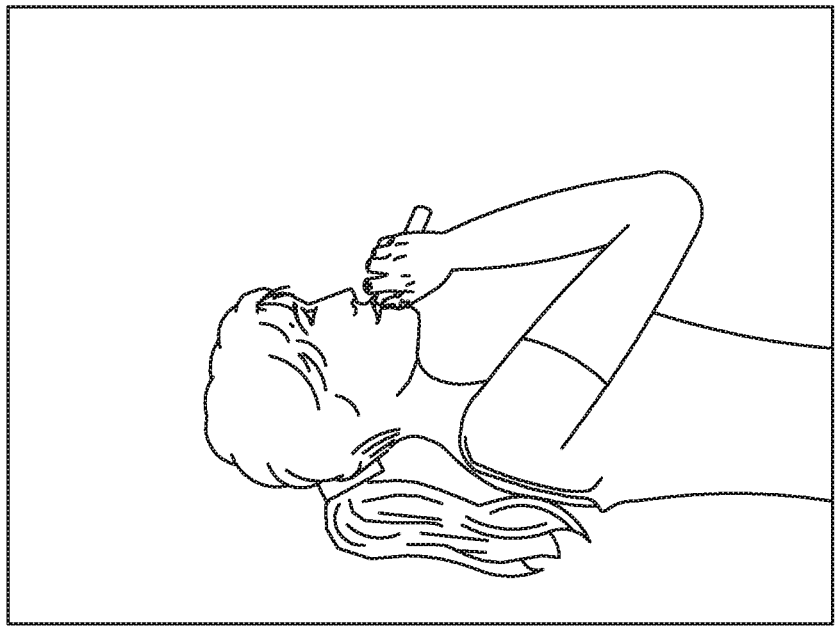
FIGS. 11-14 are photographs showing execution of an example method for saliva collection and treatment.
Figure 11:
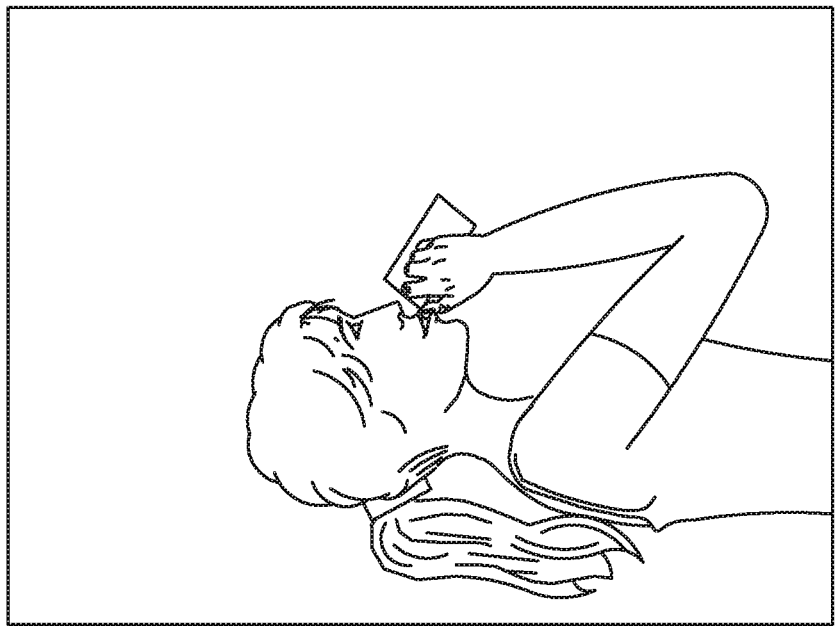
Figure 14:
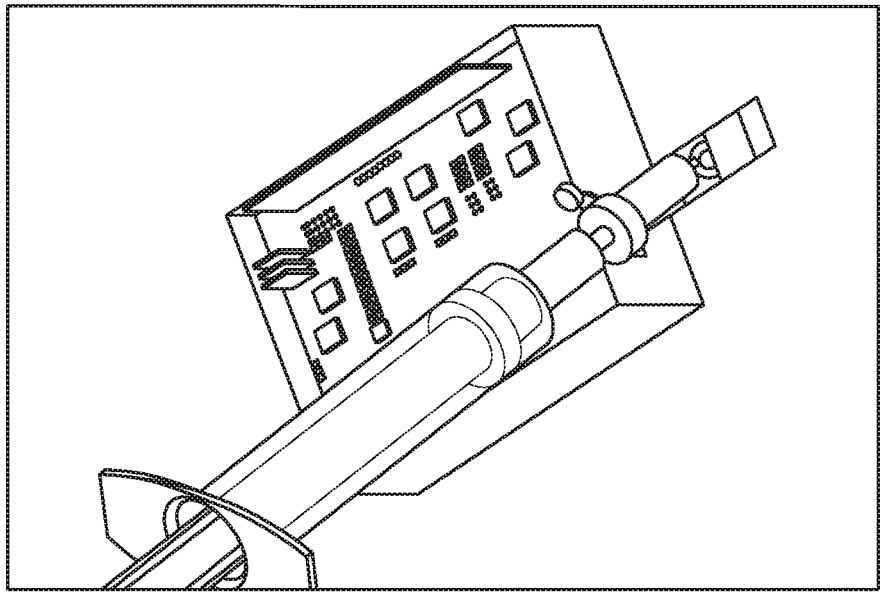
Figure 13:
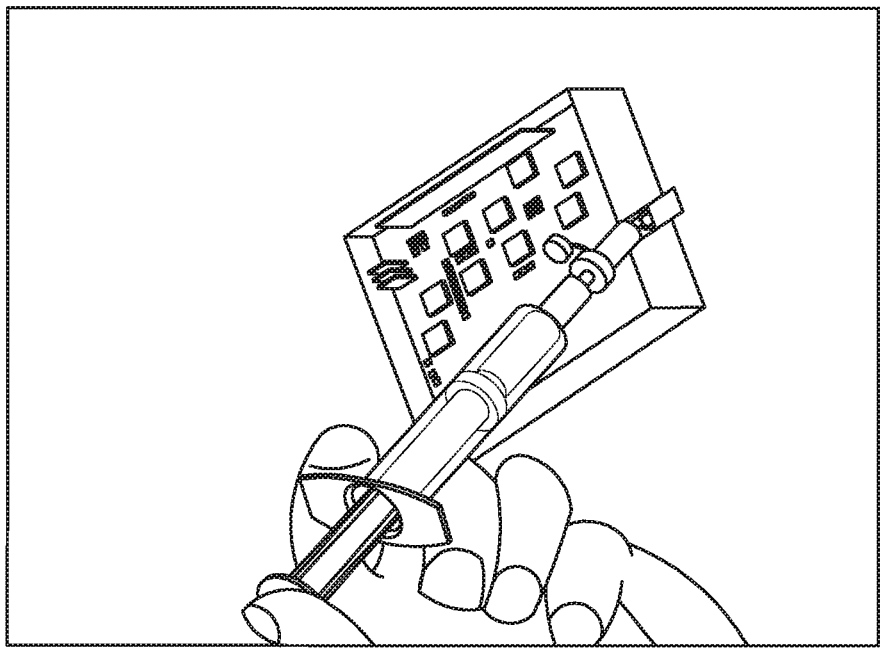

FIG. 11 shows saliva collection by a Salimetrics oral swab, which is placed in the mouth for 1 minute. FIG. 12 shows the saliva soaked swab being placed within the syringe with treatment chamber attached to the end of the syringe. FIG. 13 shows how, using the syringe, saliva is squeezed out of the swab and pushed into the chamber. FIG. 14 shows how treated saliva is then placed on a sensor for testing.

Figure 15:
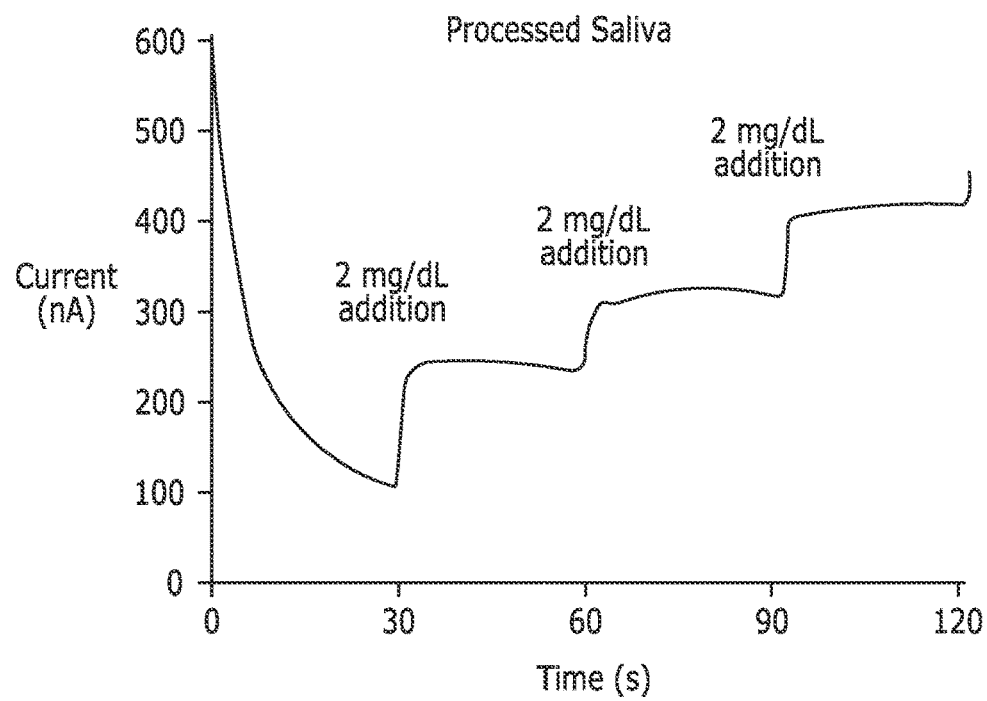
FIG. 15 is a plot showing detection of glucose in saliva processed according to the example method for saliva collection and treatment.
Figure 16:
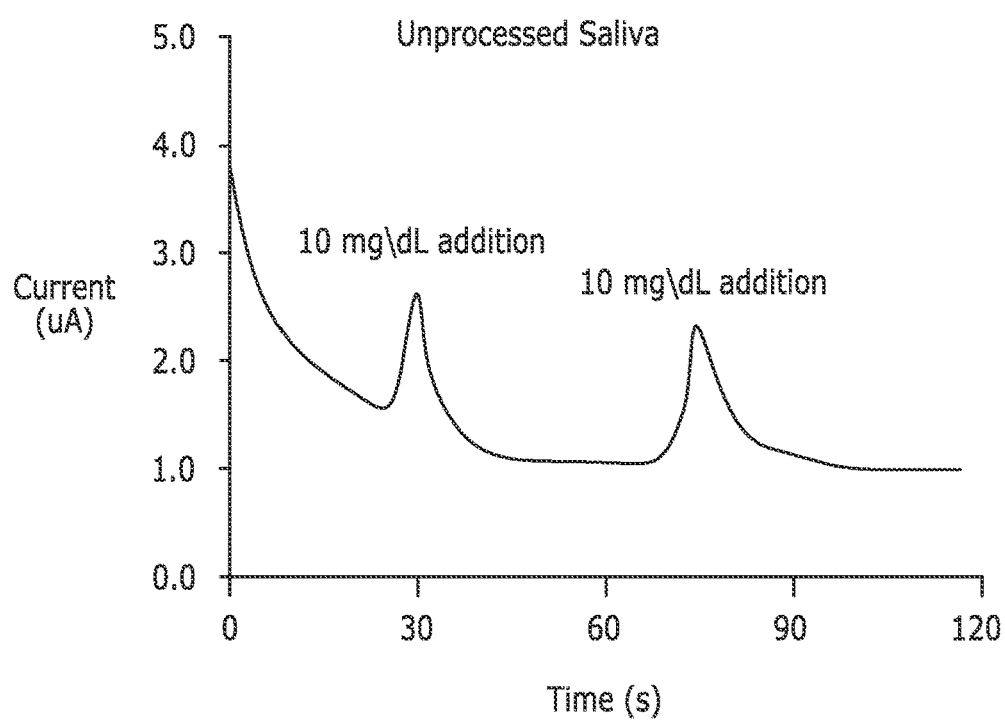
FIG. 16 is a plot showing detection of glucose in saliva that has not been processed according to the example method for saliva collection and treatment.

FIGS. 15 and 16 show results of glucose detection in treated and untreated saliva. FIG. 15 shows stable glucose detection with the collection and treatment process described herein. The glucose detection of FIG. 15 is linear with concentration leading to reliable detection of glucose. In contrast, FIG. 16 shows that untreated saliva leads to unstable detection with current degrading rapidly, making glucose detection impossible. Additionally, when 10 mg/dL of glucose was added to the treated and untreated saliva, a standard glucose assay detected about 7 mg/dL in the processed saliva and about 3 mg/dL in the unprocessed sample.

From the above description, those skilled in the art will perceive improvements, changes and modifications. Such improvements, changes and modifications are within the skill of one in the art and are intended to be covered by the appended claims.

The following is claimed:

1. A method comprising:
   collecting a biofluid sample, wherein the biofluid sample comprises water, an analyte and at least one additional component that has a negative effect on detection of the analyte in the biofluid sample;
   adding the biofluid sample to a media, wherein the media comprises a carbon-containing material;
   mixing the biofluid sample and the media, wherein the media eliminates at least a portion of the at least one additional component from the biofluid sample;
   filtering the media from the biofluid sample,
   wherein the mixing and/or the filtering uses a mechanical mechanism; and
   providing the biofluid sample for analysis, wherein the analysis comprises the detection of the analyte in the biofluid sample.

2. The method of claim 1, wherein the carbon-containing material eliminates at least a portion of the at least one additional component and/or another material that facilitates ion exchange within the biofluid sample to inhibit at least another portion of the at least one additional component.

3. The method of claim 2, wherein the carbon-containing material comprises activated charcoal, activated carbon, carbon black, graphite, graphene, oxidized graphene, and/or reduced graphene.

4. The method of claim 1, wherein the biofluid sample comprises a bodily fluid.

5. The method of claim 4, wherein the bodily biofluid comprises tears, saliva, urine, serum, plasma, and/or blood.

6. The method of claim 1, further comprising detecting an amount of the analyte in the biofluid sample using an enzyme-based process.

7. The method of claim 6, wherein the enzyme-based process detects the amount of the analyte in the biofluid sample using a colorimetric detection mechanism, a photometric detection mechanism or an electrochemical detection mechanism.

8. The method of claim 1, wherein the carbon-containing material is bound to and/or bound within at least a portion of the media.

9. The method of claim 8, wherein at least the portion of the media comprises at least one of a ceramic material, a metallic material, a polymer material, and a paper material.

10. The method of claim 1, wherein the filtering comprises passing the media and the biofluid sample through a physical filter membrane to remove the media from the biofluid sample.

11. The method of claim 10, wherein the physical filter membrane comprises cellulose acetate (CA), polyvinylidene fluoride (PVDF), Teflon, nylon, paper, and/or glass.

12. The method of claim 1, wherein the mechanical mechanism is centrifugal force, pressure, and/or flow.

13. A system comprising:
   a sample collection component configured to collect a biofluid sample, wherein the biofluid sample comprises an analyte and at least one additional component;
   a mixing component comprising a media comprising a carbon-containing material, wherein the mixing component is configured such that upon adding the biofluid sample to the mixing component, the biofluid sample mixes with the media and the media removes at least a portion of the at least one additional component;
   a filter component configured to filter the media from the biofluid sample, wherein the biofluid sample is provided to an analysis component after the media is filtered from the biofluid sample to detect the analyte in the biofluid sample.

14. The system of claim 13, wherein the carbon-containing material eliminates at least a portion of the at least one additional component in the biofluid sample and/or another material that facilitates ion exchange within the biofluid sample to inhibit at least another portion of the at least one additional component.

15. The system of claim 13, wherein the at least one additional component that a negative effect on detection of the analyte in the biofluid sample.

16. The system of claim 15, wherein the analysis component is configured to perform the detection of the analyte in the biofluid sample.

17. The system of claim 13, wherein the mixing component and/or the filter component employs a mechanical mechanism, wherein the mechanical mechanism is centrifugal force, pressure, and/or flow.

18. The system of claim 13, wherein the sample collection component comprises a cup, a swab, or a foam to collect the biofluid sample.

19. The system of claim 13, wherein the carbon-containing material is bound to and/or bound within at least a portion of the media,
wherein at least the portion of the media comprises at least one of a ceramic material, a metallic material, a polymer material, and a paper material.

20. The system of claim 13, wherein the filter component comprises a physical filter membrane to remove the media from the biofluid sample,
wherein the physical filter membrane comprises cellulose acetate (CA), polyvinylidene fluoride (PVDF), Teflon, nylon, paper, and/or glass.

* * * * *